United States Patent

Farella et al.

[11] 4,202,345
[45] May 13, 1980

[54] APPARATUS FOR DELIVERING AND RECEIVING RADIOACTIVE GAS

[75] Inventors: Ralph Farella, Scarsdale, N.Y.; Barry Dansky, Fairfield, Conn.; Leonard Epifano, Rye, N.Y.

[73] Assignee: Medi-Ray, Inc., Tuckahoe, N.Y.

[21] Appl. No.: 859,028

[22] Filed: Dec. 9, 1977

[51] Int. Cl.² ................................................ A61B 6/00
[52] U.S. Cl. ...................................... 128/654; 55/387; 128/659; 128/716
[58] Field of Search ............... 128/2 A, 2.08, 145.6, 128/145.8, 654, 659, 716, 725; 250/303, 363 S; 55/71, 74, 186, 193, 387

[56] References Cited

U.S. PATENT DOCUMENTS

| | | | |
|---|---|---|---|
| 3,666,955 | 5/1972 | Suprenant et al. | 128/2.08 X |
| 3,803,802 | 4/1974 | Schröter et al. | 55/74 X |
| 3,881,463 | 5/1975 | LeMon | 128/2 A |
| 3,976,050 | 8/1976 | Glasser et al. | 128/2 A |

FOREIGN PATENT DOCUMENTS 562625   5/1957   Italy .......................................... 55/387

*Primary Examiner*—Richard T. Stouffer
*Attorney, Agent, or Firm*—Martin Novack

[57] ABSTRACT

An apparatus for delivering and receiving gas to and from a patient, such as for lung ventilation studies. In accordance with the invention there is provided a restrictive breathing chamber adapted for coupling to the patient's breathing organs. A system, including a first check valve, is provided for coupling the breathing chamber to an inflatable gas receptacle so as to allow flow only toward the inflatable gas receptacle. Active gas input apparatus, including a second check valve, is also coupled to the breathing chamber, the second check valve allowing flow only toward the breathing chamber means. First and second auxiliary tubes and a gas filter are also provided. A system is provided for coupling the first auxiliary tube from the inflatable receptacle through the gas filter and to an ambient air environment. The second auxiliary tube is coupled from the inflatable receptacle to an ambient air environment. Finally, a gas pump is switchably coupled as between the first and second auxiliary tubes and operative to selectively cause gas flow in the first auxiliary tube toward the ambient environment, and in the second auxiliary tube toward the inflatable receptacle. A gas trap structure is also disclosed.

8 Claims, 5 Drawing Figures

4,202,345

APPARATUS FOR DELIVERING AND RECEIVING RADIOACTIVE GAS

BACKGROUND OF THE INVENTION

This invention relates to diagnostic equipment and, more particularly, to an apparatus useful in performing lung ventilation studies using radioactive gas.

Pulmonary ventilation studies have become a very useful diagnostic aid. Typically, a source of radioactive gas, such as radioactive xenon gas, is provided to a patient through a breathing tube. When the patient has inhaled the gas, a scintillation detector is used to obtain an image of the lung by detecting the presence of the radioactivity on a positional basis. In this manner, a physician can obtain useful information such as the degree to which inhaled gases are reaching the small passageways in the lungs.

Relatively elaborate and complex systems have been devised for delivering the radioactive gas to the patient and for receiving the exhaled gas and disposing of it safely. A number of considerations must be taken into account when designing such a machine. For example, when the patient is coupled to the gas delivery system, it is desirable that he be constrained to breathe only from the delivery unit, so provision is generally made for covering the mouth and nose with a mask such that ambient air cannot be inhaled. Since it is necessary for the patient to breathe during the setup and preparation periods, a source of oxygen is provided in the gas delivery system, the source being a part of the system which can be switched in, by appropriate valves. This can be disadvantageous, however, since the breathing of a higher than usual percentage of oxygen can temporarily affect lung function and disturb measurements which are taken shortly thereafter. Also, it is inconvenient and involves expense to provide a consumable source of oxygen in this manner.

A further problem with the prior art arises from the necessity of disposing of the radioactive gas without subjecting technical personnel to undue exposure or allowing exhausted gas to interfere with subsequent measurements. In most existing equipment provision is made for coupling the system's exhaust port to an external gas trap through which the exhaust gases are diverted to an appropriate conduit and eventually released outside the building. This is inconvenient in that it necessitates coupling to an external exhaust system which may or may not be available. Also, most existing gas traps for this purpose are not efficient enough to allow gas which has passed through them to exhaust into the room without possible harmful effects. These considerations are further complicated somewhat by the fact that the patient does not expel all of the radioactive gas in one breath. Rather, during a "washout" phase of operation, the patient breathes air or oxygen and the exhaust gas is only eliminated to the point desired after several breaths.

It is an object of this invention to overcome the prior art problems such as those set forth and to generally provide a combination delivery and exhaust system for radioactive gas ventilation studies.

SUMMARY OF THE INVENTION

The present invention is directed to an apparatus for delivering and receiving gas to and from a patient, such as for lung ventilation studies. In accordance with the invention there is provided a restrictive breathing chamber means adapted for coupling to the patient's breathing organs. Means, including a first check valve, are provided for coupling the breathing chamber means to an inflatable gas receptacle so as to allow flow only toward the inflatable gas receptacle. Active gas input means, including a second check valve, are also coupled to the breathing chamber means, the second check valve allowing flow only toward the breathing chamber means. First and second auxiliary tubes and a gas filter are also provided. Means are provided for coupling the first auxiliary tube from the inflatable receptacle through the gas filter and to an ambient air environment. The second auxiliary tube is coupled from the inflatable receptacle to an ambient air environment. Finally, gas pump means are switchably coupled as between the first and second auxiliary tubes and operative to selectively cause gas flow in the first auxiliary tube toward the ambient environment, and in the second auxiliary tube toward the inflatable receptacle.

In a preferred embodiment of the invention, the gas filter is a novel design of gas trap which comprises a rectangularly shaped enclosure having a removable side. A first plurality of spaced parallel panels extend from one side of the enclosure adjacent the removable side toward the side opposite said one side and abutting three sides of the enclosure, the first plurality of panels being proportioned to be spaced from said opposite side. A second plurality of spaced parallel panels parallel to the members of the first plurality are interspaced therebetween. The second plurality of parallel panels abuts three sides of the enclosure and are proportioned to be spaced from said one side. Adsorbing particles, such as charcoal, substantially fill the enclosure, and a pair of apertures in the ends of the enclosure parallel to the panels is provided as inlet and outlets ports.

In accordance with the disclosed invention, no consumable source of oxygen need be provided. Also, an internally contained subsystem eliminates the problems associated with used radioactive gas without the need for providing external elimination means. These advantages are obtained in a compact self-contained portable unit.

Further features and advantages of the invention will become more readily apparent from the following detailed description when taken in conjunction with the accompanying drawing.

DESCRIPTION OF THE PREFERRED EMBODIMENT

Figure 1:
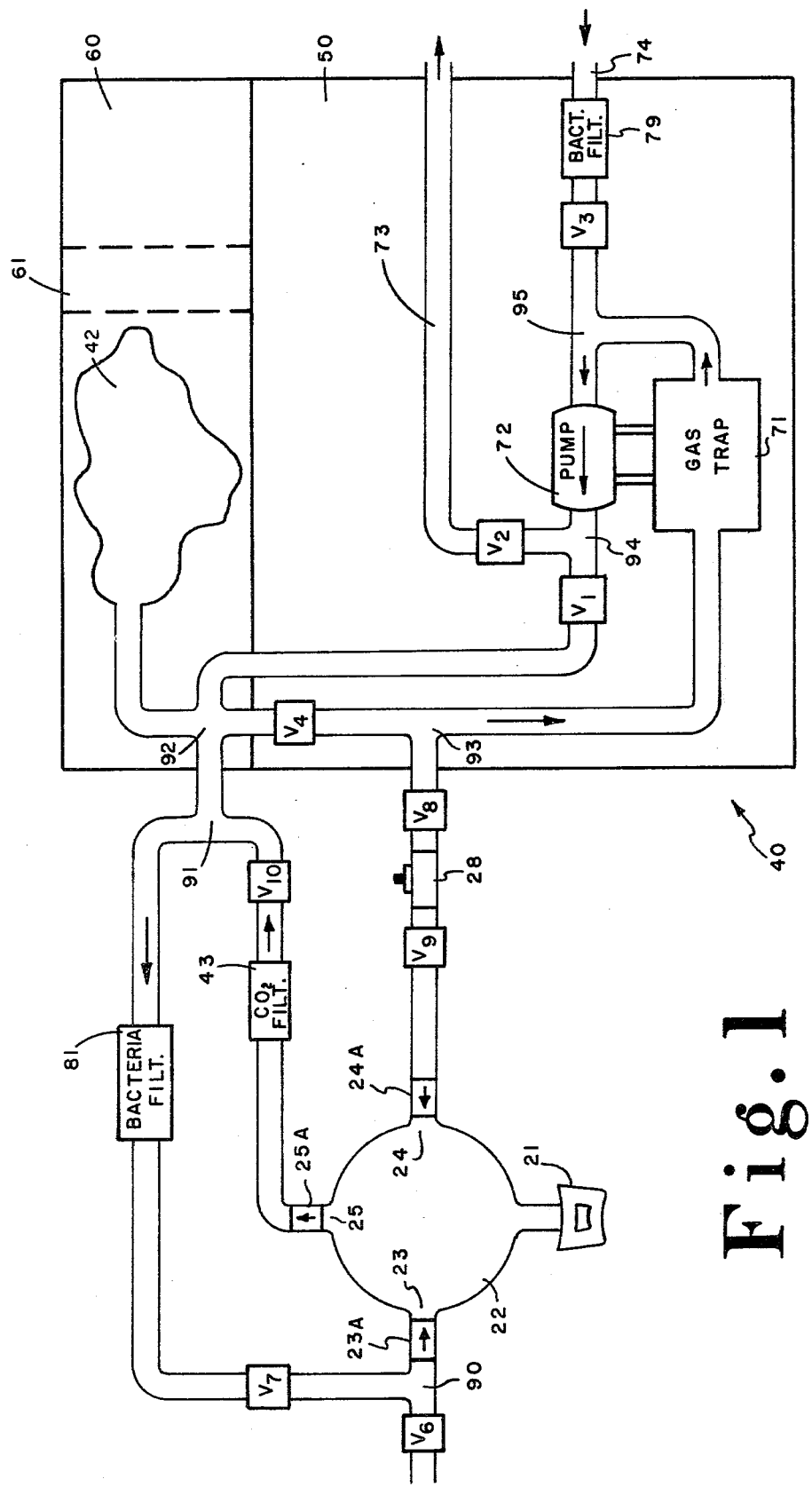
FIG. 1 is a schematic view of an apparatus in accordance with the invention for delivering and receiving radioactive gas to and from a patient.

Referring to FIG. 1, there is shown an embodiment of an apparatus for delivering and receiving gas to and from a patient for lung ventilation studies or the like. A breathing mask 21 is adapted for placement over the patient's nose and mouth and confines the patient's breathing to the equipment. A breathing chamber 22, coupled to the mask 21 by a tube, has a pair of inlet ports 23 and 24 and an outlet port 25. These ports have check valves, designated by reference numerals 23A, 24A and 25A respectively, associated therewith and serving to confine the flow of gas to the desired inlet or outlet direction. The inlet port 23 is coupled, via a three-way coupling 90 and a valve $V_6$, to the room air environment. The inlet port 23 is also coupled to an inflatable receptacle or bag 42 in a console 40, the path being via one leg of coupling 90, a valve $V_7$, a bacteria filter 81, a three-way coupling 91 and a four-way coupling 92. The outlet port 25 is coupled via carbon dioxide filter 43 and couplings 91 and 92 to the inflatable bag 42. The other inlet port 24 is coupled via a valve $V_9$ to an in-line active gas cannister 28 which is, in turn, coupled to the inflatable bag 42 via a valve $V_8$, a three-way coupling 93, a valve $V_4$, and four-way coupling 92.

The console 40, shown schematically in FIG. 1, is typically mounted on wheels (not shown), and the tubes coupled between the console and the breathing mask can be routed through a movable "arm" (not shown) which is known in the art and useful in adjusting the height and position of the breathing mask to accommodate a patient in a lying or sitting position, as desired. The console 40 has separate lower and upper compartments 50 and 60, respectively. The upper compartment 60, which houses the bag 42, has a front access door (not shown) which is sealable in an airtight manner such that a spirometer 61 can be employed in conjunction therewith in known fashion.

The lower compartment 50 of console 40 includes a compact gas trap 71, to be described, and an air pump 72 which may be mounted on the gas trap. A first auxiliary tube 73 and a second auxiliary tube 74 are each coupled to the ambient room environment. The auxiliary tube 73 is coupled through a valve $V_2$ to a three-way coupling 94, one branch of which is coupled to the outlet end of the pump 72, and the other branch of which is coupled through a valve $V_1$ and coupling 92 to the inflatable receptacle 42. The tube 74 is coupled through a bacteria filter 79 and a valve $V_3$ to a three-way coupling 95, one branch of which is coupled to the inlet end of pump 72 and the remaining branch of which is coupled to the outlet end of gas trap 71. The inlet end of the gas trap 71 is coupled to the inflatable receptacle 42 via coupling 93, valve $V_4$, and coupling 92.

In general terms, operation of the equipment is as follows: the receptacle 42 is first filled with a predetermined amount of air which the patient will breathe when fully contrained to breathe on the equipment. To achieve this, valves $V_1$ and $V_3$ are opened and all other valves are closed. The pump 72 is actuated and room air is pumped through the tube 74, the bacteria filter 79 and through the valves $V_3$ and $V_1$, and finally to the receptacle 42. When the receptacle 42 has been filled to a desired degree, the pump 72 is inactivated.

When the breathing mask 21 is first put on the patient, inhalation may initially be of room air (valve $V_6$ temporarily opened), but the patient is shortly thereafter put on "machine" air by opening valve $V_7$ and closing valve $V_6$. Now, the patient will inhale air from receptacle 42 which passes through the bacteria filter 81, valve $V_7$, and the check valve 23A. Exhalation into receptacle 42, in both cases, is via check valve 25A, carbon dioxide filter 43 and valve $V_{10}$.

In the present embodiment the radioactive gas is in a commercially available cannister 28 which is inserted in-line between the valves $V_8$ and $V_9$. The cannister is ruptured, after insertion, to release the gas into the line, within the confines of the valves $V_8$ and $V_9$. At an appropriate time, the valves $V_9$, $V_8$ and $V_4$ are opened and the patient inhales the active gas along with air from the bag 42. The camera (not shown) is activated while the patient holds his or her breath. The patient next "rebreathes" into receptacle 42 via $CO_2$ filter 43 and valve $V_{10}$ and from receptacle 42 via bacteria filter 81 and valve $V_7$.

To eliminate remaining radioactive gas in the patient's lungs, the valve $V_6$ is opened and the valve $V_7$ is closed so that the patient inhales room air and exhales into receptacle 42. At this point, valves $V_2$ and $V_4$ can be opened and air pump 72 activated. The gas in receptacle 42, which includes the radioactive gas, is drawn, via valve $V_4$, through the gas trap 71, pump 72, and the valve $V_2$, and eventually exhausted through auxiliary tube 73.

Figure 4:
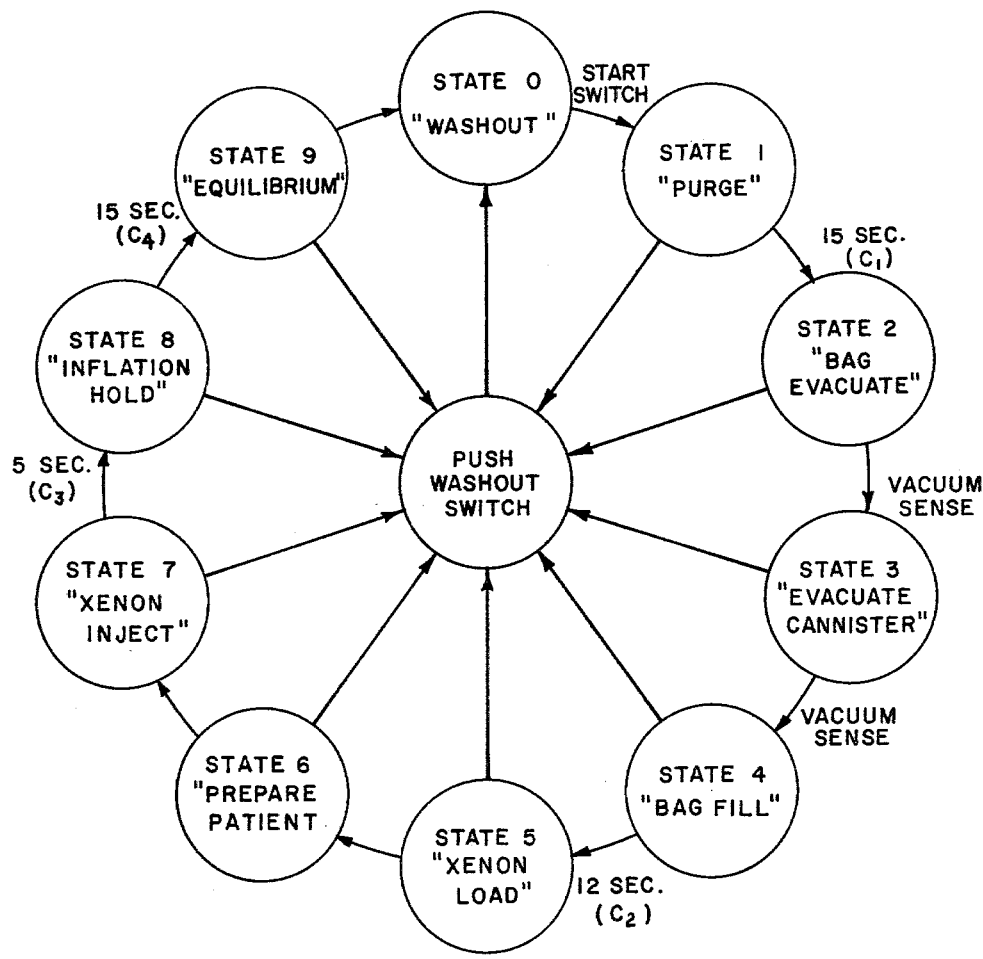
FIG. 4 is a state diagram which illustrates the state sequence generated by the ROM of FIG. 3.
Figures 3, 5:
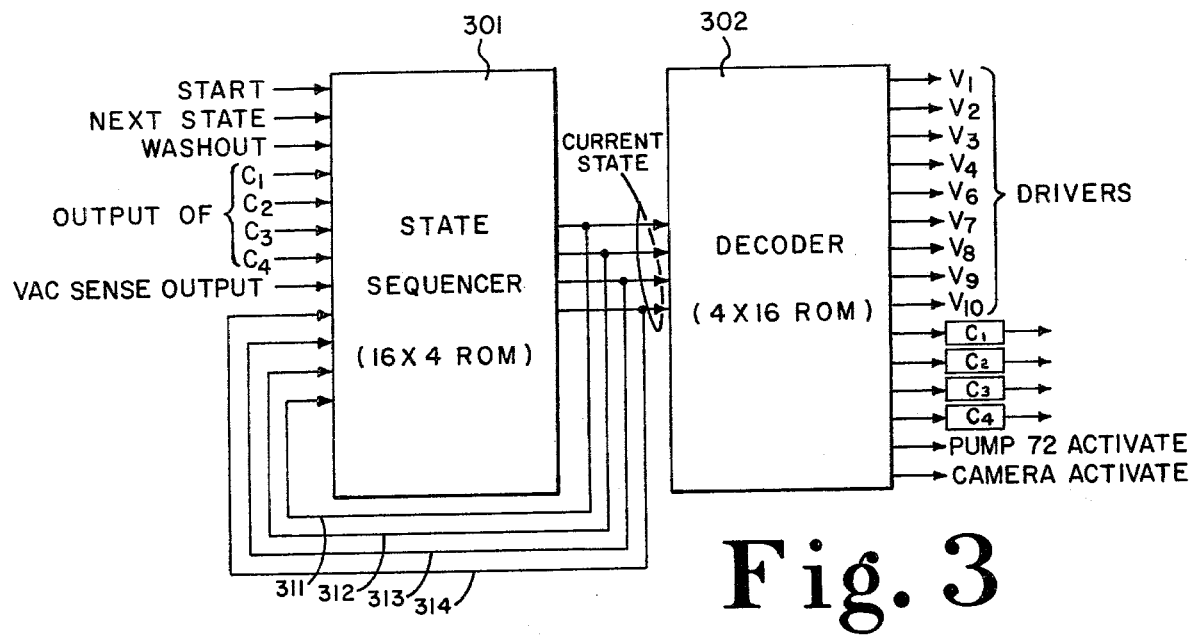
FIG. 3 is a block diagram of control circuitry for the apparatus of FIG. 1.
FIG. 5 is a logic truth table which defines and shows the status of the output lines of decoder 302 of FIG. 3.

The apparatus of FIG. 1 is preferably, although not necessarily, operated semi-automatically in accordance with an aspect of the invention described in conjunction with FIGS. 3, 4 and 5. In particular, a partially automatic sequence of operations, in accordance with the state diagram of FIG. 4, is controlled by the circuitry of FIG. 3. The circuitry of FIG. 3, which is preferably housed within the console 40, controls operation of the apparatus of FIG. 1 by opening or closing electrically-operable valves $V_1$ through $V_{10}$, and activating or inactivating the pump 72. Automatic operation of a camera (not shown), utilized to record an image of the active gas in the patient's respiratory system, is also achieved as part of the prescribed sequence.

Referring to FIG. 3, a state sequencer module 301 and a decoder module 302 are provided. In the present embodiment, the state sequencer 301 is a 16×4 read-only memory (ROM) of which twelve inputs are utilized, and the decoder 302 is a 4×16 ROM of which fifteen outputs are utilized. The four output lines of the state sequencer 301 each carry a binary output, and the signals on these lines define the status of the equipment. In the present embodiment, there are ten possible equipment statuses (of course, 16 possible statuses are available from four output lines, but only 10 of the 16 are utilized herein). The current state of the state sequencer is fed back to four of the inputs thereof, via lines 311–314. The state sequencer utilizes the current state of these four lines, in conjunction with the signal levels on its other twelve input lines, to generate a new state. The decoder 302 is responsive to each state to produce control signals on its output lines, the binary condition of each output line, for each state, being defined by the truth table of FIG. 5. In particular, the outputs of decoder 302 control the valves $V_1$ through $V_{10}$, the pump 72, and enable timers designated $C_1$ through $C_4$. The timers $C_1$ through $C_4$ have different characteristic times and, each timer, after being enabled produces an output after its characteristic time has elapsed. The outputs of the clocks are four of the inputs to the state sequencer 301. Three additional inputs to the state sequencer 301 are voltage levels coupled via switches (such as pushbutton switches—not shown) on the console 40. One of the switches is a "Start" switch which initiates a normal sequence of operations. Another switch controls a binary signal which indicates "Next State" and allows an operator to switch to the next state of a sequence without necessarily waiting for a particular condition to occur or for a particular time to elapse. Another pushbutton switch allows the operator to enter the state known as "Washout" from any state, as will be discussed below. A further input to the state sequencer is the output of a vacuum sensor 351.

A typical sequence of operation will now be described. The pushing of the Start switch causes state 1 (actually "0001" in binary notation—but decimal notation will be utilized in the text for ease of explanation) to be entered, this being simply done by programming the state sequencer ROM 301 to produce the output "0001" whenever a signal appears on the "start" input line, regardless of the signals on other input lines. State 1 is designated as "Purge" and is a state wherein outside air is drawn through the previously used (for the last patient) active gas cannister 28 and exhausted to the outside via the gas trap 71. The condition of various components during state 1 can be seen from the truth table of FIG. 5. In the table, a logical "0" means that a valve is opened or that a pump or camera is activated or a timer enabled, whereas a logical "1" means that a valve is closed or that a pump or timer is inactivated. As seen from the table, during state 1 valves $V_2$, $V_6$, $V_8$ and $V_9$ are opened and pump 72 is on. All other valves are closed. Accordingly, ambient air is drawn in through $V_6$ and then through the spent cannister 28 (via $V_8$ and $V_9$), and then exhausted to the outside via the gas trap 71, pump 72, and $V_2$. As seen from the truth table of FIG. 5, the initiation of state 1 also sets the timer $C_1$ which controls operation of the Purge state (state 1) to continue for a predetermined time, for example 15 seconds. At the end of the fifteen second period, timer $C_1$ generates an output which is received at an input line of state sequencer 301. The state sequencer 301 (ROM) is programmed such that when this signal occurs, in conjunction with the signal "0001" (indicating state 1) on the lines 311 through 314, it generates a new output representative of the next state, i.e. state 2 ("0010" in binary notation).

The state 2 is designated as "Bag Evacuate", and during this state the bag 42 is emptied via $V_4$, gas trap 71, pump 72 and $V_2$. State 2 continues until a vacuum is sensed by the vacuum detector 351, indicating complete evacuation of the bag 42. The detector 351 generates an output signal which is received by the state sequencer 301. The presence of this signal, in conjunction with input signals indicative of the previous states, on lines 311 through 314, causes entrance into the next state; i.e. state 3 designated "Evacuate Cannister". During this state, as seen from the truth table of FIG. 5, $V_2$ and $V_8$ are opened and pump 72 is on. State 3 is somewhat redundant with state 2 in that a vacuum is drawn, in this case including the region of the spent cannister 28. Any remaining gas or air from the cannister is drawn out via valve $V_8$, gas trap 71, pump 72, and valve $V_2$. Again, state 3 continues until sufficient vacuum is sensed in the line by vacuum detector 351. An output from the vacuum detector 351, in conjunction with the fed back state signals on lines 311 through 314, causes the ROM 301 to produce a state 4 output.

State 4 is designated as "Bag Fill", and during this state the inflatable receptacle or bag 42 is inflated with a suitable amount of air so that the patient will be able to later breath "on the machine". As seen from the truth table of FIG. 5, in state 4 valves $V_1$ and $V_3$ are opened, pump 72 is on, and timer $C_2$ is activated. The bag 42 is filled with ambient environment air via bacteria filter 79, valve $V_3$, pump 72, and valve $V_1$. Timer $C_2$ is selected, in conjunction with the pump capacity and the bag capacity, to be of sufficient duration to allow the bag 42 to be filled to a desired degree, a time of twelve seconds typically being suitable to load 10-15 liters of air.

An output of the timer $C_2$ indicates that the bag 42 has been filled to the desired degree. This timer output signal, in conjunction with the fed back state signals on lines 311 through 314, causes the state sequencer 301 to enter the next state; i.e. state 5 designated "Xenon Load". During this state, the operator typically loads a new xenon cannister 28 into the in-line connector between valves $V_8$ and $V_9$. During this state the patient can also be placed on the breathing mask 21 and will momentarily inhale room environment air via valve $V_6$, and exhale into the bag 42 via the carbon dioxide filter 43 and valve $V_{10}$ (see truth table of FIG. 5). It should be noted that the patient can alternatively be initially placed on the breathing mask during the next state.

Upon completion of the xenon loading operation, the operator pushes the "Next State" button switch and the state sequencer, in response to the next state signal and the fed back state signals on lines 311 through 314, causes entry into the next state; viz., state 6 designated as "Prepare Patient". During state 6, the patient inhales air from the bag 42 and exhales back into the bag via a carbon dioxide filter. In particular, and as can be seen from the truth table of FIG. 5, inhalation is from the bag 42 via bacteria filter 81 and valve $V_7$, and exhalation back into the bag 42 is via carbon dioxide filter 43 and the valve $V_{10}$. The patient, who typically has received prior oral instructions, is now breathing normally on the machine and is prepared to receive the xenon gas.

When the patient is just completing an exhalation, the operator pushes the "Next State" button switch (or, alternatively, a separate switch which can be marked "Xenon Inject") which, in conjunction with the current state signals on the lines 311 through 314, causes the state sequencer to enter the next state. State 7 is designated as "Xenon Inject". During this state, as seen from the truth table of FIG. 5, valves $V_4$, $V_8$ and $V_9$ are opened, and the pump 72 is off. Also, timer $C_3$ is activated. As noted, this state is initiated manually by the operator when the patient is about to inhale. Air stored in the bag 42 is inhaled along with the xenon gas from cannister 28, the route being via valves $V_4$, $V_8$ and $V_9$. The timer $C_3$ has a characteristic time interval of five second since the inhalation should take less than five seconds. After the five second interval, an output from timer $C_3$ causes the state sequencer (which, again, also receives the current state signals fed back on lines 311 through 314) to enter the next state; i.e., state 8 designated as "Inflation Hold".

The patient has been instructed beforehand to hold his or her breath as long as possible after the active gas has been inhaled, but to give the operator a manual signal if a distress condition (such as no longer being able to hold the breath) is encountered. The normal inflation hold is an additional 15 seconds. Accordingly, during state 8, and as seen from the truth table of FIG. 5, a timer $C_4$ is activated and has a characteristic time of 15 seconds. Also, all valves except $V_7$ are closed and the pump 72 is off. This means that the patient cannot exhale, although slight inhalation via valve $V_7$ is still possible. The camera (not shown) is also typically activated to take over one or more pictures during this state. If, during the "Inflation Hold" state, the patient gives a distress signal, the operator will immediately hit the "Next State" button and the next state of the sequence, state 9, will be entered.

In the normal sequence of events, an output of timer $C_4$, in conjunction with the current state signals fed back on lines 311 through 314, will cause the state sequencer 301 to enter the next state; viz., state 9 designated as "Equilibrium".

During the Equilibrium state 9, the patient inhales from the bag 42 and exhales back into the bag 42. In particular, and as seen from the truth table of FIG. 5, during state 9 the valves $V_{\cdot}$ and $V_{10}$ are opened so that inhalation from bag 42 is via bacteria filter 81 and valve $V_7$ and exhalation back into bag 42 is via $CO_2$ filter 43 and valve $V_{10}$. Additional pictures are also typically taken by the camera during this state.

After a suitable "Equilibrium" study period, the operator pushes the "Washout" button, and state 0, designated as the "Washout" state, is entered. During "Washout", and as seen from the truth table of FIG. 5, room air is inhaled via valve $V_6$ and exhalation is into bag 42 via $CO_2$ filter 43 and valve $V_{10}$. Also, as seen from the state diagram of FIG. 4, the state sequencer 301 is programmed such that the "Washout" state can be entered at any time, as a fail-safe mechanism, if the operator pushes the "Washout" pushbutton switch.

Figure 2:
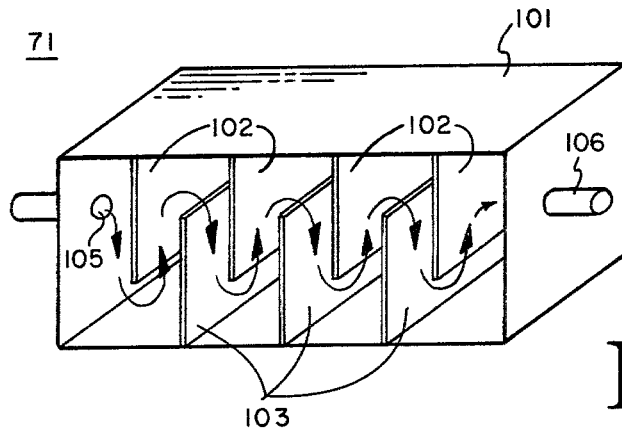
FIG. 2 is a side elevational view of a gas trap in accordance with the invention and employed in FIG. 1.

Referring to FIG. 2, there is shown a side view of the gas trap 71 with its side removable cover, which may be a flat plate, removed. A rectangularly shaped enclosure 101 is formed of a radiation shielding material. A plurality of spaced parallel panels 102 extend from one side of the enclosure adjacent the removable side (i.e., the top side in the FIGURE) toward the opposite side of the enclosure (i.e., the bottom side of the FIGURE) and abut three sides of the enclosure (including the removable side). These panels are proportioned smaller than the end dimensions of the enclosure 101 such that they are spaced from the bottom of the enclosure. A second set of spaced parallel panels, designated by reference numeral 103, are parallel to the panels 102 and interspaced therebetween. These panels also abut three sides of the enclosure, but extend from the bottom of the enclosure toward the top of the enclosure and are spaced from the top. Enclosure 101 has a pair of apertures 105 and 106 in the ends thereof, which couple to inlet and outlet tubes. Adsorbing particles, typically charcoal, fill the entire enclosure before the removable cover is replaced.

The construction of the gas trap of FIG. 2 facilitates the filling of the enclosure and yields a circuitous path through the adsorbing material (as indicated by the curved arrows) which provides sufficient adsorbing volume to render harmless the gas which is expelled from aperture 106. This is achieved utilizing the illustrated compact configuration which can be included within the console 40.

The invention has been described with reference to a particular embodiment, but it will be appreciated that variations within the spirit and scope of the invention will occur to those skilled in the art. For example, it will be understood that the valves $V_1$ through $V_6$ and the pump can be actuated manually from a control panel (not shown) on the console, or, if desired, actuated in automatic sequence.

We claim:

1. Apparatus for delivering and receiving gas to and from a patient comprising, in combination:
   restrictive breathing chamber means adapted for coupling to the patient's breathing organs;
   an inflatable receptacle;
   means including a first check valve for coupling said breathing chamber means to said inflatable gas receptacle so as to allow flow only toward said inflatable gas receptacle;
   active gas input means, also coupled to said breathing chamber means;
   first and second auxiliary tubes;
   a gas filter;
   first means for coupling said first auxiliary tube from said inflatable receptacle through said gas filter to an ambient air environment;
   second means for coupling said second auxiliary tube from said inflatable receptacle to an ambient air environment; and
   gas pump means switchably coupled in conjunction with said first and second coupling means between said first and second auxiliary tubes and operative to selectively cause gas flow from said inflatable receptacle through said first coupling means and said first auxiliary tube toward said ambient environment and from said ambient environment through said second coupling means and said second auxiliary tube toward said inflatable receptacle.

2. Apparatus as defined by claim 1 further comprising means including a second check valve for coupling said breathing chamber means to said inflatable gas receptacle so as to allow flow only toward said breathing chamber means.

3. Apparatus as defined by claim 2 wherein said restrictive breathing chamber means includes a passage coupled to the ambient air environment via a third check valve which allow flows only toward said restrictive breathing chamber means.

4. Apparatus as defined by claim 3 further comprising a plurality of electrically controllable valves in series with said first, second and third check valves and said auxiliary tubes; and electrical sequence control means for automatically controlling the state of said valves and said pump to automatically fill said receptacle, constrain the patient's breathing to the receptacle, and then exhaust the receptacle via said gas filter.

5. Apparatus as defined by claim 4 wherein said gas filter comprises:
   a rectangularly shaped enclosure having a removable side;
   a first plurality of spaced parallel panels extending from one side of said enclosure adjacent said removable side toward the side opposite said one side and abutting three sides of said enclosure, said first plurality of panels being proportioned to be spaced from said opposite side;
   a second plurality of spaced parallel panels parallel to the members of said first plurality and interspaced therebetween, said second plurality of parallel panels abutting three sides of said enclosure and being proportioned to be spaced from said one side;
   adsorbing particles substantially filling said enclosure;
   a pair of apertures in the ends of said enclosure parallel to said panels.

6. Apparatus as defined by claim 1 wherein said restrictive breathing chamber means includes a passage coupled to the ambient air environment via a further check valve which allows flow only toward said restrictive breathing chamber means.

7. Apparatus as defined by claim 1 further comprising a plurality of electrically controllable valves in series with said first check valve and said auxiliary tubes; and electrical control means for automatically controlling the state of said valves and said pump.

8. Apparatus as defined by claim 1 wherein said gas filter comprises:
- a rectangularly shaped enclosure having a removable side;
- a first plurality of spaced parallel panels extending from one side of said enclosure adjacent said removable side toward the side opposite said one side and abutting three sides of said enclosure, said first plurality of panels being proportioned to be spaced from said opposite side;
- a second plurality to spaced parallel panels parallel to the members of said first plurality and interspaced therebetween, said second plurality of parallel panels abutting three sides of said enclosure and being proportioned to be spaced from said one side;
- adsorbing particles substantially filling said enclosure;
- a pair of apertures in the ends of said enclosure parallel to said panels.

* * * * *